United States Patent
Barker

(10) Patent No.: US 7,377,922 B2
(45) Date of Patent: May 27, 2008

(54) TRANSFER RING FOR OFFSET TAPERED 3D CONNECTOR

(75) Inventor: B. Thomas Barker, Bartlett, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 550 days.

(21) Appl. No.: 10/824,752

(22) Filed: Apr. 15, 2004

(65) Prior Publication Data

US 2005/0234450 A1 Oct. 20, 2005

(51) Int. Cl.
*A61B 17/56* (2006.01)

(52) U.S. Cl. .................................... 606/61

(58) Field of Classification Search ............ 606/60, 606/61; 403/384, 388, 398
See application file for complete search history.

(56) References Cited

U.S. PATENT DOCUMENTS

| | | | |
|---|---|---|---|
| 4,170,990 A | 10/1979 | Baumgart et al. | |
| 4,198,081 A | 4/1980 | Harrison et al. | |
| 4,880,343 A | 11/1989 | Matsumoto | |
| 4,987,892 A | 1/1991 | Krag et al. | |
| 5,047,029 A * | 9/1991 | Aebi et al. | 606/61 |
| 5,053,034 A | 10/1991 | Olerud | |
| 5,246,443 A | 9/1993 | Mai | |
| 5,290,289 A | 3/1994 | Sanders et al. | |
| 5,366,331 A | 11/1994 | Erbes | |
| 5,411,523 A | 5/1995 | Goble | |
| 5,505,731 A | 4/1996 | Tornier | |
| 5,540,689 A | 7/1996 | Sanders et al. | |
| 5,551,871 A | 9/1996 | Besselink et al. | |
| 5,562,661 A * | 10/1996 | Yoshimi et al. | 606/61 |
| 5,584,695 A | 12/1996 | La Sachdeva et al. | |
| 5,586,983 A | 12/1996 | Sanders et al. | |
| 5,624,440 A | 4/1997 | Huebner | |
| 5,643,262 A * | 7/1997 | Metz-Stavenhagen et al. | 606/61 |
| 5,643,263 A * | 7/1997 | Simonson | 606/61 |
| 5,643,264 A | 7/1997 | Sherman et al. | |
| 5,645,544 A | 7/1997 | Tai et al. | |
| 5,645,599 A | 7/1997 | Samani | |
| 5,681,135 A | 10/1997 | Simonson | |
| 5,709,685 A | 1/1998 | Dombrowski et al. | |
| 5,741,225 A * | 4/1998 | Lax et al. | 604/22 |
| 5,885,285 A | 3/1999 | Simonson | |
| 5,947,967 A * | 9/1999 | Barker | 606/61 |
| 5,976,135 A | 11/1999 | Sherman et al. | |

(Continued)

*Primary Examiner*—Eduardo Robert
*Assistant Examiner*—Michael J. Araj
(74) *Attorney, Agent, or Firm*—Woodard, Emhardt, Moriarty, McNett & Henry LLP

(57) ABSTRACT

Embodiments of a device and method for connecting a bone fastener, for example a spinal screw, to an elongated member are disclosed. In one embodiment, a body having channels to receive the fastener and elongated member is tapered and has an aperture for a locking member. A tapered washer slides over the body. The tapered washer has an inner diameter that is smaller than part of the tapered portion of the body allowing it to engage the body. The fastener passes through the body and engages the washer. An offsetting member slides over the body. The body slides over the elongated member and the offsetting member offsets the elongated member from the spinal fastener and contacts each in two differing locations. A locking member is inserted into a threaded aperture in the body to apply a compressive force that compresses all of the members preventing relative motion of the components.

25 Claims, 5 Drawing Sheets

U.S. PATENT DOCUMENTS

| | | |
|---|---|---|
| 6,004,323 A | 12/1999 | Park et al. |
| 6,056,753 A | 5/2000 | Jackson |
| 6,183,473 B1 | 2/2001 | Ashman |
| 6,187,005 B1 * | 2/2001 | Brace et al. .................. 606/61 |
| 6,210,413 B1 * | 4/2001 | Justis et al. .................. 606/61 |
| 6,234,705 B1 | 5/2001 | Troxell |
| 6,248,107 B1 | 6/2001 | Foley et al. |
| 6,334,733 B1 * | 1/2002 | Tyson ........................ 403/388 |
| 6,402,749 B1 | 6/2002 | Ashman |
| 6,471,703 B1 | 10/2002 | Ashman |
| 6,520,962 B1 | 2/2003 | Taylor et al. |
| 6,520,990 B1 | 2/2003 | Ray |
| 6,562,038 B1 | 5/2003 | Morrison |
| 6,572,618 B1 | 6/2003 | Morrison |
| 6,579,292 B2 | 6/2003 | Taylor |
| 6,623,485 B2 * | 9/2003 | Doubler et al. ............... 606/61 |
| 2002/0013585 A1 | 1/2002 | Gournay et al. |

* cited by examiner

TRANSFER RING FOR OFFSET TAPERED 3D CONNECTOR

FIELD OF THE INVENTION

This invention relates generally to the field of orthopedic implant systems, particularly to systems of the type that employ fasteners engaged to elongated members. More particularly, the invention concerns a connector that provides variable angle adjustability between a fastening element and the elongated member while allowing ease of assembly.

BACKGROUND OF THE INVENTION

Several systems have been developed for the use in correcting and stabilizing orthopedic injuries or deformities and promoting bone fusion. For example, in systems intended for the spine, an elongated member, commonly in the form of a bendable rod, can be longitudinally disposed adjacent the vertebral column and is fixed to various vertebrae along the length of the column by way of a number of spinal fasteners. A variety of spinal fasteners can be used, such as hooks, bone bolts and screws, each configured to engage a specific portion of the vertebrae.

An example of a spinal fixation system of this type is the TSRH® Spinal System. In this product, spinal hooks and bone screws are engaged to a spinal rod by way of eyebolts. The eyebolts and associated clamping nut provide a three-point shear clamp that positively locks the hook or screw element to the spinal fixation rod.

The TSRH® Spinal System, sold by Medtronic Sofamor Danek, includes connectors allowing variable angular, height, and axial orientations between the elongated members and the spinal fasteners. One example of such a connector is disclosed in U.S. Pat. No. 5,947,967. Embodiments of that connector allow degrees of freedom of movement in an infinitely variable fashion to help reduce difficulties in placing implants prior to and during manipulation of the spine. Such freedom during installation tends to make implantation significantly easier.

Under some conditions, a degree of back-out of the spinal fasteners can occur in some spinal systems after installation. In some cases, such back-out does not affect the performance of the implants. In other cases, however, performance of the implants may be lessened, and additional surgery may be necessary to secure or replace implant parts. Accordingly, a connecting member, such as a connector for the spine, that combines a wide range of freedom of movement between it and a fastener, with assistance in preventing back-out of fasteners after installation and simple assembly during surgery would be desirable.

DESCRIPTION OF THE PREFERRED EMBODIMENTS

Figure 1:
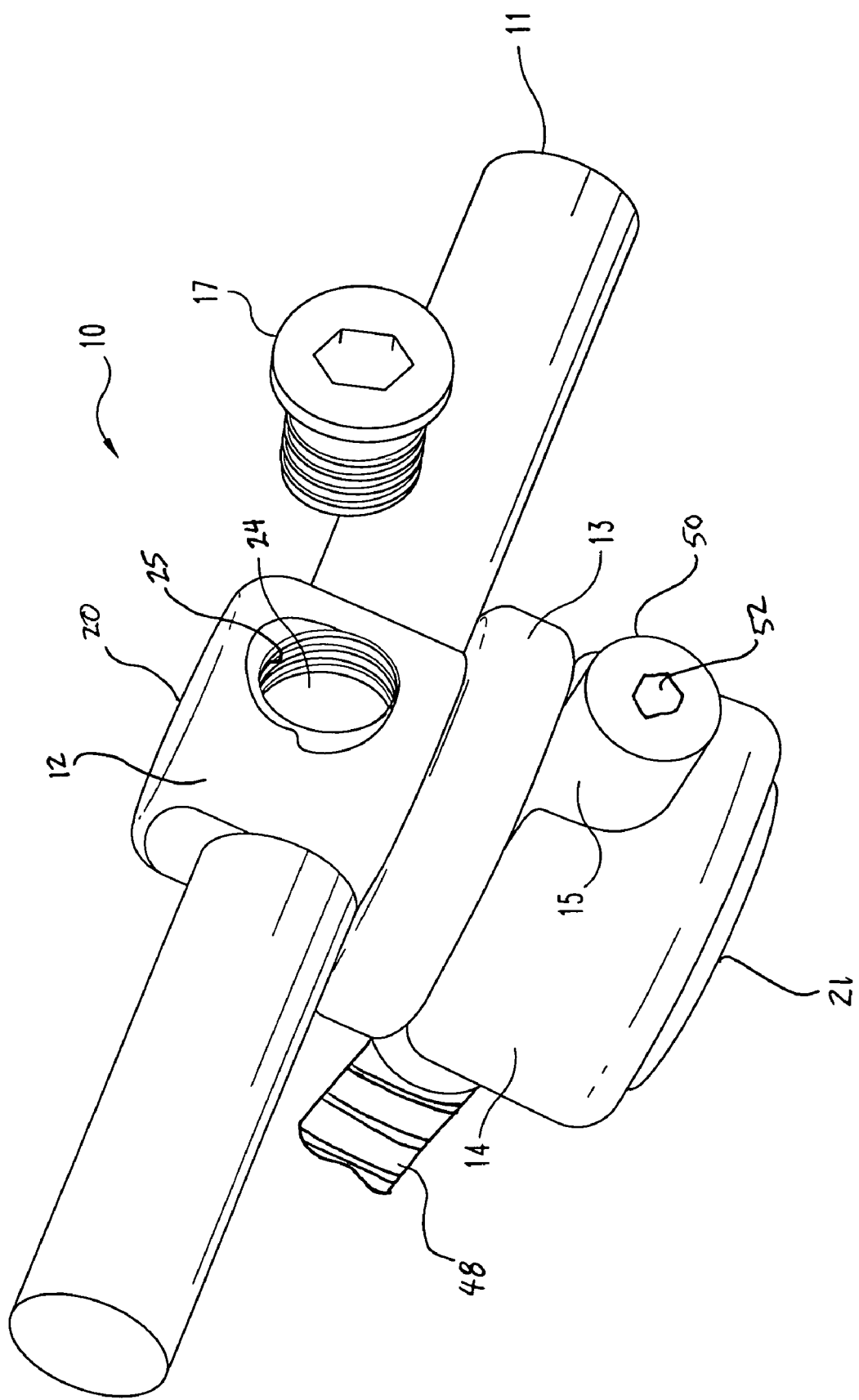
FIG. 1 is a perspective view of an embodiment of a spinal connection device.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations, modifications, and further applications of the principles of the present invention as illustrated being contemplated as would normally occur to one skilled in the art to which the invention relates.

In accordance with one embodiment of the present invention, FIG. 1 shows a connection device 10 for connecting an elongated member 11 and a bone fixation member 15 together. This embodiment will be described in the context of a spinal usage, although other usages for this and other embodiments may be possible. This embodiment of connection device 10 includes an offset body 12, offsetting member 13, and washer 14. Elongated member 11 and bone fixation member 15 pass through offset body 12, in a particular embodiment in substantially perpendicular directions. Offsetting member 13 contacts or is connected to elongated member 11 and bone fixation member 15 in at least two locations, thereby leaving some distance between offsetting member 13 and washer 14.

Elongated member 11 is an elongated spinal rod in one embodiment, such as the rod used with the TSRH® Spinal System. Such a rod can be relatively smooth, or can be partially or entirely roughened or textured as by knurling, shot peening, threading or other methods. Other forms of elongated member 11 are contemplated, such as other types of spinal rods or plates, or similar structures for use with other bones or tissues. For example, elongated member 11 could constitute a bar or a portion of spinal plate.

Figure 2:
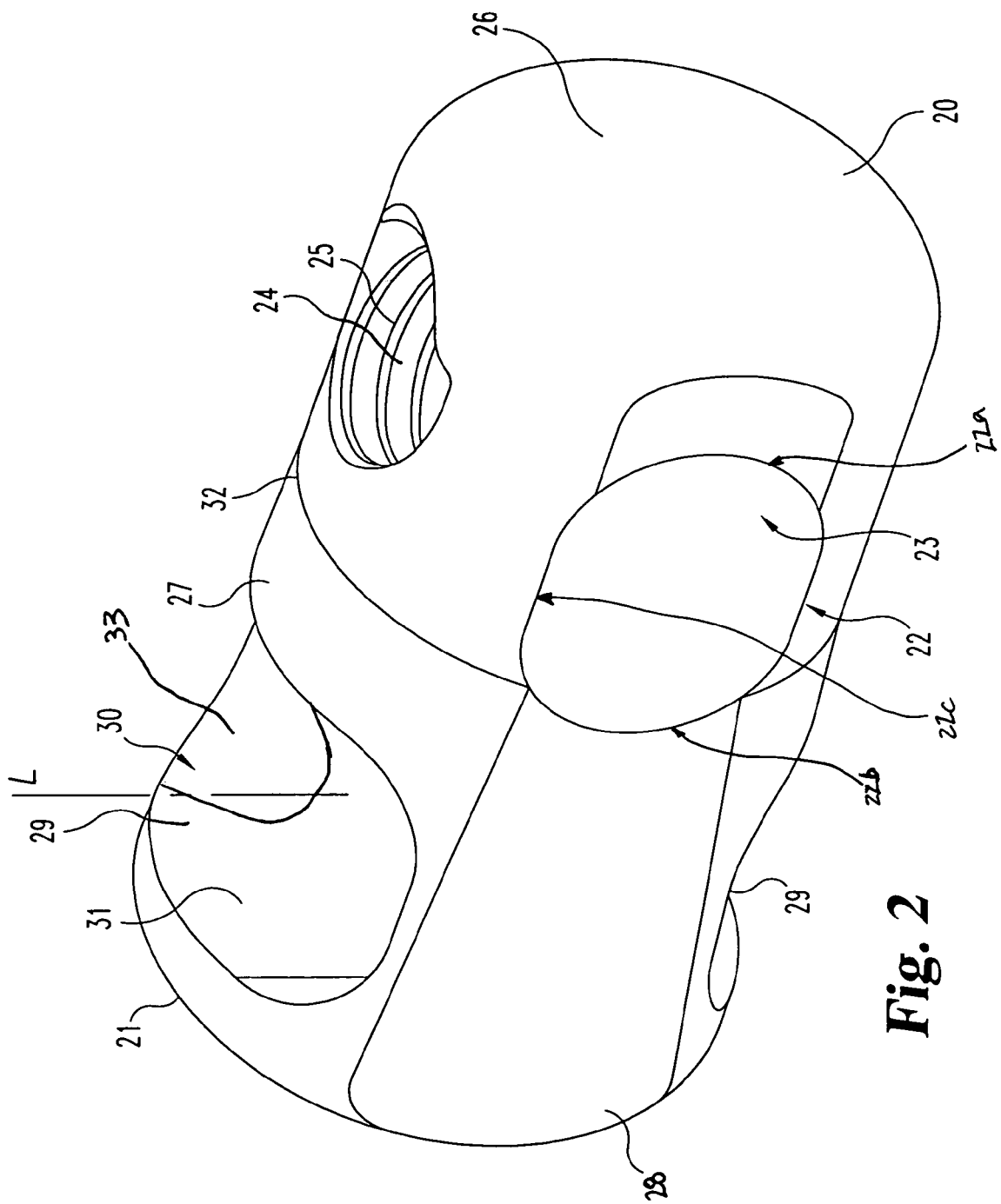
FIG. 2 is a perspective view of an embodiment of an offset body useful in the spinal connection device illustrated in FIG. 1.
Figure 3:
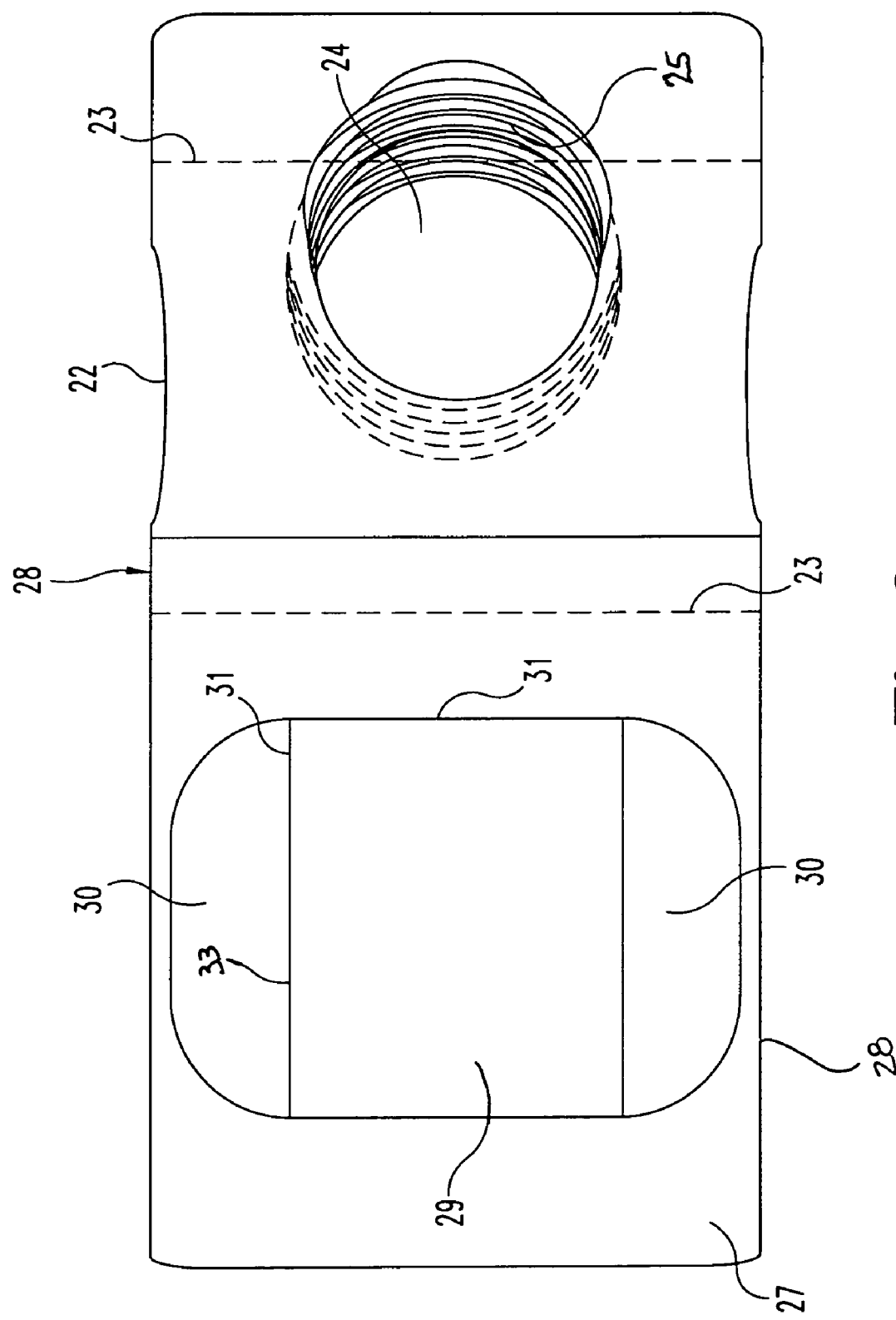
FIG. 3 is a top plan view of the embodiment of the offset body illustrated in FIG. 2.

Referring generally to FIGS. 1-3, the illustrated embodiment of offset body 12 has a first end 20 and a second end 21. Traveling from first end 20 towards the second end 21 the circumference of the body 12 gradually increases from a middle part of offset body 12 towards second end 21. Various differing body formations are contemplated for other embodiments of offset body 12. For example, offset body 12 may continuously taper from first end 20 towards second end 21. Conversely, offset body 12 may have a steep increase in diameter over a short length of the body. Alternatively, offset body 12 may be tapered along somewhat less, somewhat more, or substantially its entire length.

In the illustrated embodiment, offset body 12 includes a channel 22 that passes through the offset body 12. Channel 22 is sized and configured to receive elongated member 11, and is bounded at least in part by surface 23. Channel 22 preferably includes a radius at its ends 22a, 22b separated by a section 22c having two parallel lines forming an oval-like shape with rounded ends and a substantially straight length. This creates an elongated channel 22 so that offset body 12 and elongated member 11 may translate with respect to each other. In other embodiments, channel 22 may have other dimensions and shapes, such as tapering between ends 22a, 22b. In a particular embodiment, channel 22 is connected to an aperture 24, which can be oriented at an angle to a surface of offset body 12. Aperture 24 accommodates a locking member 17 so that locking member 17 can apply a force against elongated member 11 disposed within channel 22.

Aperture 24, in a particular embodiment, includes threads 25 to accommodate a locking member 17 that is threaded, e.g. a set screw. Additional apertures may be included as alternative places to fit locking member 17, or to accommodate additional locking members.

Offset body 12 can also include a first outer surface area 26 and a second outer surface area 27. First outer surface area 26, in the illustrated embodiment, is smaller in diameter than the second outer surface area 27. Offset body 12 begins to taper out and increase in circumference beginning at edge 32 towards second end 21. In this embodiment, the circumference of the tapered end is at the maximum at second end 21. The diameter of second outer surface area 27 will be greater at one or more points than the diameter of the inner surface of washer 14. This configuration allows washer 14 to be slidably mountable over offset body 12. In a particular embodiment, offset body 12 also contains flat surfaces 28 on either side of offset body 12. Flat surfaces 28 improve the gripping of the offset body 12 and increase in width as tapering of offset body 12 increases towards second end 21.

Offset body 12 may also contain a second channel 29. Channel 29 in one embodiment is at least partially bounded by inner surfaces 30 and sized for receiving bone fixation member 15 and may have various configurations. Inner surfaces 30 are curved and run from the second outer surface area 27 near flattened areas 28 towards the center of offset body 12. A second set of inner surfaces 31, if provided, can form a box-like shape, which passes through the entire offset body 12 on all four sides. However, other arrangements of inner surfaces 30 and/or 31 within or about channel 29 are contemplated. For instance, one of inner surfaces 30 at the upper portion of offset body 12 can be set at a different angle than the angle of an opposite inner surface 30. Channel 29 may assume a "bow tie"-like shape as inner surfaces 30 diverge from second inner surfaces 31. In that embodiment, channel 29 begins with a wide opening along second outer surface area 27 and narrows toward the center. As can be seen in FIG. 3, first inner surfaces 30 begin along the curve of the outer surface area 27 and pass down to where they eventually become a straight edge 33 at second inner surfaces 31. In addition, in this embodiment, the second inner surfaces 31 run parallel with first end 20 and second end 22 and pass directly through offset body 12. Bone fixation member 15 can sweep through equal angles in either direction from a vertical line L passing through channel 29.

Figure 4:
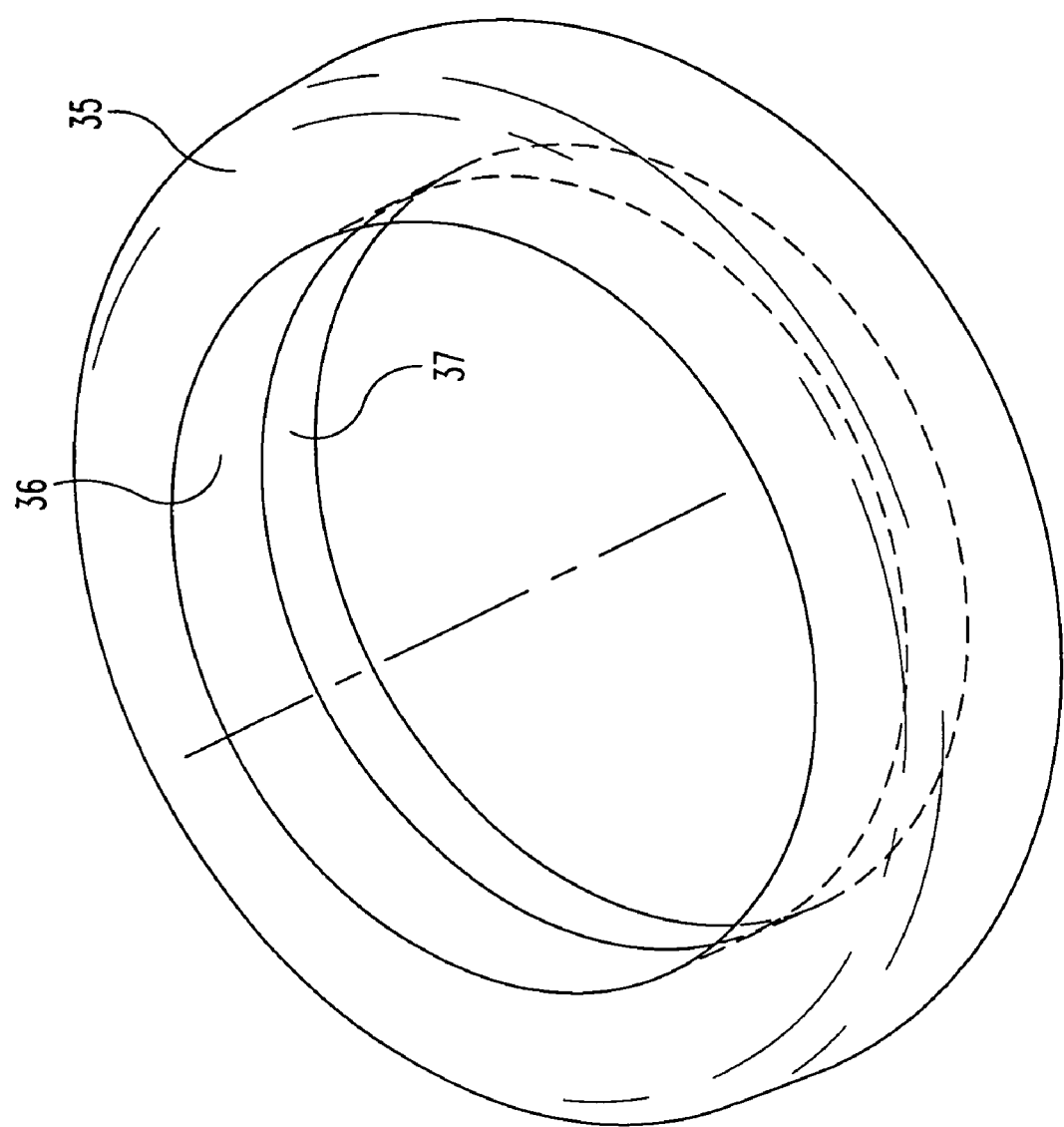
FIG. 4 is a perspective view of an embodiment of an offsetting member useful in the spinal connection device illustrated in FIG. 1.

Referring now to FIG. 4, an embodiment of offsetting member 13 is shown in more detail. Offsetting member 13 has a ring shape, but any suitable shape that is slidable over offset body 12 is contemplated. Offsetting member 13 has an outer surface 35, a first inner surface 36 and second inner surface 37. First inner surface 36 and second inner surface 37 are preferably formed to catch the tapered end of offset body 12 and fix firmly to offset body 12 because of an interference fit between at least one of surfaces 36, 37 and at least one of outer surfaces 26, 27 of body 12. In an alternate embodiment, offsetting member 13 is grooved. This embodiment enables fixation member 15 to contact offsetting member 13 along a greater area thereby increasing the frictional forces that assist in the inhibition of the backing out of fixation member 15. Offsetting member 13 may be composed of a shape memory alloy. The shape memory alloy may expand or contract in relation to temperature depending upon the composition of the alloy. A shape memory alloy that expands at least in the thickness of offsetting member 13 upon a change from room temperature to human body temperature assists in fixing all components and helps prevent or limit backing out of bone fixation member 15. One example of a shape memory alloy that may be used is Nitinol, an alloy of almost equal atomic parts of nickel and titanium. This material is rigid in a higher temperature phase and flexible in a lower temperature phase, and is also biocompatible. Other biocompatible materials, such as titanium, stainless steel, sturdy plastics, and the like can also be used.

Figure 6:
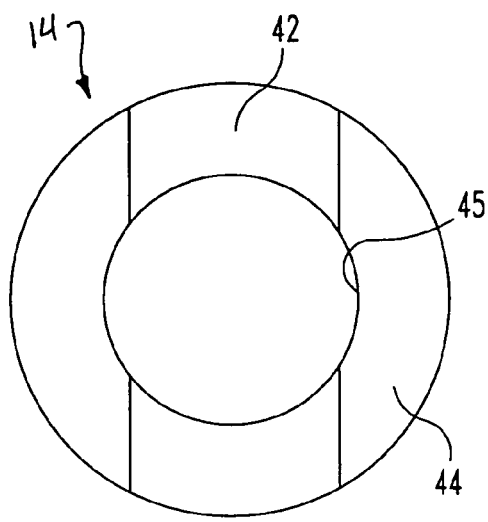
FIG. 6 is a top view of an embodiment of a washer useful in the spinal connection device illustrated in FIG. 1.
Figure 5:
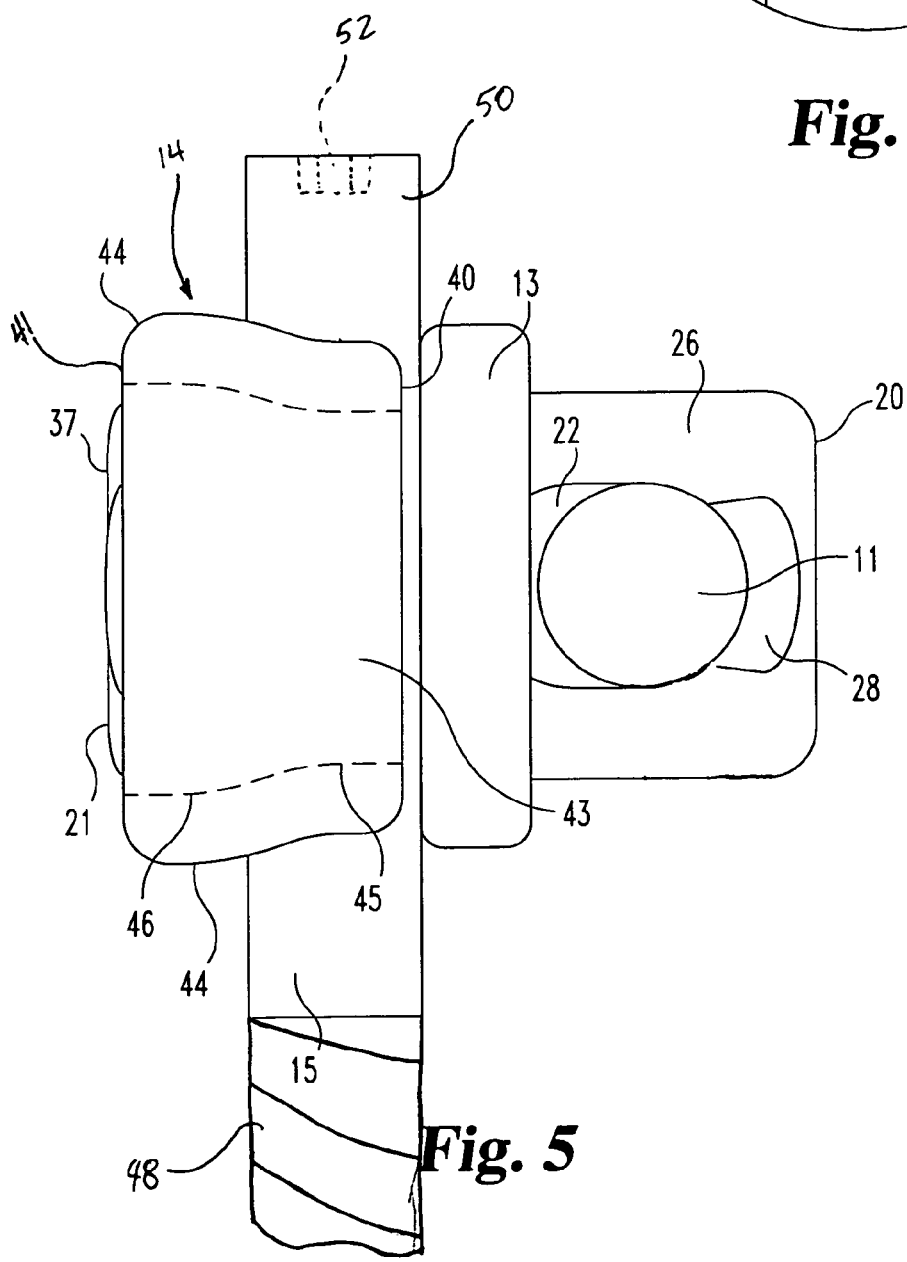
FIG. 5 is a top view of the embodiment of a spinal connection device illustrated in FIG. 1.

Referring now generally also to FIGS. 5-6, an embodiment of washer 14 is shown. Washer 14 has a first end 40 and a second end 41 as well as a first outer surface 43 and second outer surface 44. In this embodiment, the second outer surface 44 increases in diameter towards second end 41. The diameter of first outer surface 43 is smaller than the diameter of second outer surface 44. Washer 14 may also have a circular first inner surface 45 of a smaller diameter than a second inner surface 46. In a particular embodiment, the slope of second outer surface 44 and the slope from the transition between inner surface 45 and outer surface 46 is the same. Alternatively, it is contemplated that these slopes can differ in other embodiments. The circumference of washer 14 can increase from first inner surface 45 to second outer surface 44. Further, at least part of the inner diameter of washer 14 is smaller than at least part of the outer diameter of offset body 12. Inner surfaces 45 and 46 and second outer surface 44 allow washer 14 to be slidably mountable to offset body 12. For example, washer 14 can easily slide over first end 20 of offset body 12 and catch the tapered second end 21, forming an interference fit between inner surface 45 (and possibly inner surface 46) of washer 14 and a portion of outer surface area 27 of offset body 12.

Washer 14 can also include a groove 42 running along first end 40. Groove 42 may be configured to engage bone fixation member 15 along the length of groove 42. Groove 42 may be constructed to allow bone fixation member 15 to extend outside of groove 42 slightly. Such a construction allows offsetting member 13 to contact bone fixation member 15 directly in at least two differing locations. Other designs allowing offsetting member 13 to contact bone fixation member 15 in at least two differing locations are contemplated by the present invention.

Bone fixation member 15, in one embodiment, is a bone screw such as a Schantz-type bone screw. Bone fixation member 15 can include a threaded portion 48 for connection to a bone, such as a vertebra, and a substantially cylindrical upper portion 50. Upper portion 50 may include a print 52, shown in the illustrated embodiment as an internal hexagonal print. Other prints, such as internal slots or hexalobes or external prints, could also be used. Further, other types of bone fixation members can be used with or engaged by connector 10. For example, bone fixation member 15 could constitute or include a hook, threaded bolt, clamp or similar holding device.

As previously noted, a fixation member 17, which in one embodiment is or includes a set screw, is provided. Fixation member 17 is inserted into second aperture 24 of offset body 12 to firmly fix together offset body 12, offsetting member 13, washer 14 screw 15, and elongated member 11.

Connector assembly 10 permits connection of bone fixation member 15 to elongated member 11 at infinitely variable angular orientations and infinitely variable axial or height orientations. For example, in a typical rod-screw instrumentation of the spine, the rod extends along a length of the spine with the screw extending anteriorly into a portion of a vertebra. The relative angular orientation is then substantially in the sagittal plane of the spine. Variable axial or height adjustment is intended to accommodate different locations of the elongated member relative to the underlying vertebra. For instance, in some situations, it is not possible to contour the elongated member sufficiently so that the member is always the same distance posteriorly from each of the instrumented vertebrae. Adjustment in axial position or height allows the connector to accommodate this dimensional variation and still interconnect fixation member 15 to elongated member 11.

The use of connection device 10 will now be described in connection with spinal surgery as one example. It will be appreciated that connection device 10 could be used in other parts of the body, if desired. Initially, the patient is prepared for surgery as usual. An incision is made in the patient relatively proximate to the intended location of the implant. If an "open" incision is made, i.e. a relatively large incision for direct access to the implant site, then retraction of muscle or other tissue may be necessary. If a minimally invasive incision is used, i.e. one in which the size of the incision is minimal, tubes or other access devices can be inserted through the incision to a position adjacent the implant site, so that instruments and implants can be inserted to the implant site. The implant site is prepared as the surgeon desires.

Prior to or after the incision is made and the implant site prepared, washer 14 is slid over first end 20 of offset body 12. Washer 14 is at first loosely disposed about offset body 12 and free to rotate to meet an orientation of bone fixation member 15. For example, washer 14 can be rotated around offset body 12 until groove 42 of washer 14 is aligned with apertures 29 of offset body 12. Bone fixation member 15 is then passed through body 12 via apertures 29, and groove 42 of washer 14 is adjacent to bone fixation member 15.

Offsetting member 13 is slid over the first end 20 of offset body 12 and in one embodiment contacts bone fixation member 15 in at least two places. Elongated member 11 is inserted into channel 22 of offset body 12, or offset body 12 is placed around elongated member 11 so that part of elongated member 11 is within channel 22 of offset body 12. Relative movement between the bone fixation member 15 and elongated member 11 in multiple degrees of freedom is possible. First, the offset body 12 itself can be rotated around the elongated member 11 about the longitudinal axis of the member. Additional degrees of freedom, such as the variability of the position of connection device 10 along the length of fixation member 15, may exist. The relative angle between bone fixation member 15 and elongated member 11 may also be varied.

On the location of connection device 10 into a desired position, the surgeon can fix the implant together by inserting fixation member 17 into aperture 24. As noted previously, fixation member 17 can be a set screw that is screwed into a threaded aperture 24. In other embodiments, the parts of connection device 10 can be fixed with clamps or other fixing devices. Inserting fixation member 17 (e.g. set screw) into threaded aperture 24 allows fixation member 17 to contact and apply a compressive force against the side of elongated member 11. Elongated member 11 may translate across channel 22, and contacts offsetting member 13. Offsetting member 13 may slide along offset body 12, and contacts the portion of bone fixation member 15 that extends beyond groove 42 in washer 14 in at least two locations. Fixation member 15 applies a compressive force against washer 14, which may cause washer 14 to slide along offset body 12 until inner surface 45 engages the tapered second end 21 of offset body 12. Thus, bone fixation member 15 and elongated member 11 are firmly fixed with respect to each other, and connection device 10 is fixed with respect to elongated member 11.

The above describes structures are preferably made of biocompatible materials. Such materials may include stainless steel, titanium, alloys such as nickel-titanium alloys (e.g. Nitinol), and/or certain sturdy plastics.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method, comprising:
   connecting an elongated member to a connection member, said connection member having a first channel and a second channel, so that at least part of said elongated member occupies at least part of said first channel;
   sliding an offsetting member over said connection device so that at least a part of said offsetting member is between at least a part of said first channel and at least a part of said second channel;
   connecting a bone fixation member to said connection member so that at least part of said bone fixation member occupies at least part of said second channel; and
   applying compressive force to said elongated member, said offsetting member, and said bone fixation member, wherein said offsetting member contacts said elongated member and said bone fixation member in at least two differing locations.

2. The method of claim 1, wherein said offsetting member has a ring shape.

3. The method of claim 1, wherein said offsetting member further includes at least two differing inner diameters.

4. The method of claim 1, wherein said offsetting member is composed of a shape memory alloy.

5. The method of claim 1, wherein said offsetting member further includes at least one groove.

6. A connection device for connecting a spinal fastener to an elongated member comprising:
   a body having a first end, a second end, a first channel, a second channel, and a third channel, said body having a portion that tapers outwardly towards said second end;
   a washer slidably mountable over said body, said washer having a groove and an inner surface, wherein said inner surface has a diameter smaller than a diameter of the tapered portion of said body;
   an offsetting member slidable over said first end, wherein said offsetting member contacts said spinal fastener in at least two locations; and
   a fixation member insertable in said third channel, wherein the fixation member applies a compressive force preventing relative notion between the spinal fastener and the elongated member, wherein the entirety of said offsetting member is between a central longitudinal axis of the spinal fastener and a central longitudinal axis of the elongated member.

7. The apparatus of claim 6, wherein a portion of said body extends through said offsetting member.

8. The apparatus of claim 6, wherein said offsetting member further includes at least two differing inner diameters.

9. The apparatus of claim 6, wherein said offsetting member further includes at least one groove.

10. The apparatus of claim 6, wherein said fixation member is a set screw.

11. The apparatus of claim 6, wherein said body member has a flat surface on either side of said body member.

12. The apparatus of claim 6, wherein said washer has a first outer surface and a second outer surface, said first outer surface having a diameter that is smaller than a diameter of said second outer surface.

13. The apparatus of claim 6, wherein said offsetting member has a ring shape.

14. The apparatus of claim 6, wherein said offsetting member is composed of a shape memory alloy.

15. The apparatus of claim 6, wherein said fastener includes a threaded member.

16. The apparatus of claim 6, wherein said fastener is a Schanz-type screw.

17. The apparatus of claim 6, wherein said fastener includes a hook.

18. The apparatus of claim 6, wherein said fastener includes a clamp.

19. A method, comprising:
   providing a body having a first end, a second end, a first channel, a second channel, and an aperture, wherein a portion of said body tapers outwardly;
   sliding a washer over said body;
   passing a fastener through said body via said first channel; and
   sliding an offsetting member over said body, wherein said offsetting member engages said fastener in at least two locations;
   placing said body over said elongated member via said second channel; and
   inserting a locking member into said aperture thereby locking said fastener with respect to said elongated member,
   wherein said washer has an opening, and said sliding of said washer includes having said washer opening substantially perpendicular to said first channel.

20. The method of claim 19, wherein said offsetting member has a ring shape.

21. The method of claim 19, wherein said offsetting member further includes at least two differing inner diameters.

22. The method of claim 19, wherein said offsetting member is composed of a shape memory alloy.

23. The method of claim 19, wherein said offsetting member further includes at least one groove.

24. The method of claim 19, wherein said locking member is a set screw, and said aperture is a threaded bore and intersects said second channel.

25. The method of claim 24, wherein said threaded bore is arranged at an angle relative to a line between said first channel and said second channel.

* * * * *